(12) United States Patent
Dietz (10) Patent No.: US 11,324,414 B2
(45) Date of Patent: May 10, 2022

(54) DEVICES, SYSTEMS AND METHODS FOR CONTROLLING A SPRING FORCE EXERTED ON A SENSOR FOR OBTAINING BIO-CONDUCTANCE READINGS USING A LINEAR ACTUATOR

(71) Applicant: Vine Medical LLC, Saint George, UT (US)

(72) Inventor: Phillip W. Dietz, Saint George, UT (US)

(73) Assignee: Vine Medical, LLC, Saint George, UT (US)

(*) Notice: Subject to any disclaimer, the term of this patent is extended or adjusted under 35 U.S.C. 154(b) by 460 days.

(21) Appl. No.: 16/203,437

(22) Filed: Nov. 28, 2018

(65) Prior Publication Data

US 2020/0163576 A1    May 28, 2020

(51) Int. Cl.

| A61B 5/053 | (2021.01) |
| A61H 39/02 | (2006.01) |
| A61B 5/0531 | (2021.01) |
| A61B 5/0532 | (2021.01) |
| A61B 5/251 | (2021.01) |
| A61B 5/00 | (2006.01) |

(52) U.S. Cl.
CPC ............ *A61B 5/053* (2013.01); *A61B 5/0531* (2013.01); *A61B 5/0532* (2013.01); *A61B 5/251* (2021.01); *A61B 5/442* (2013.01); *A61B 5/6843* (2013.01); *A61B 5/6885* (2013.01); *A61B 2562/16* (2013.01); *A61B 2562/225* (2013.01); *A61H 39/02* (2013.01); *A61H 2201/5061* (2013.01); *A61H 2230/65* (2013.01); *A61H 2230/655* (2013.01)

(58) Field of Classification Search
CPC ..... A61B 5/053; A61B 5/0531; A61B 5/0532; A61B 5/251; A61B 5/6843; A61B 5/6885; A61B 5/442; A61B 2562/16; A61B 2562/225; A61B 2090/064; A61B 2090/065; A61H 39/02; A61H 2230/65; A61H 2230/655; A61H 2201/5061
See application file for complete search history.

(56) References Cited

U.S. PATENT DOCUMENTS

| 4,608,987 | A | 9/1986 | Mills | |
| 7,536,220 | B2* | 5/2009 | Horne | A61B 5/0531 |
| | | | | 600/547 |
| 8,386,027 | B2* | 2/2013 | Chuang | A61B 18/14 |
| | | | | 600/547 |
| 8,682,425 | B2* | 3/2014 | Larsen | A61H 39/002 |
| | | | | 600/548 |
| 2008/0202233 | A1 | 8/2008 | Lan | |

(Continued)

*Primary Examiner* — Devin B Henson
(74) *Attorney, Agent, or Firm* — Terrence J. Edwards; TechLaw Ventures, PLLC (57) ABSTRACT

A probe device provides an enhanced bioelectric and spring-loaded sensing tip with an integrated force sensor. The probe device measures the bioelectric conductance value from a patient for therapeutic and/or diagnostic purpose using the spring-loaded sensing tip. In addition, the probe device measures the force applied by the spring-loaded sensing tip against the patient using the integrated force sensor. Using feedback from the force sensor and the bioconductive data of the patient, the force applied at the spring-loaded sensing tip may be adjusted to obtain improved results.

20 Claims, 8 Drawing Sheets

(56) References Cited

U.S. PATENT DOCUMENTS

2013/0137951 A1    5/2013   Chuang et al.
2016/0157816 A1    6/2016   Denny
2016/0278699 A1    9/2016   Freeman et al.

* cited by examiner

DEVICES, SYSTEMS AND METHODS FOR CONTROLLING A SPRING FORCE EXERTED ON A SENSOR FOR OBTAINING BIO-CONDUCTANCE READINGS USING A LINEAR ACTUATOR

TECHNICAL FIELD

The disclosure relates to obtaining bioelectric information and readings from a patient. In particular, the disclosure relates to devices, systems, and methods for providing and using an enhanced probe with a pressure sensor to facilitate locating and obtaining a bioelectric conductance value from a patient for assessment, therapeutic and/or diagnostic purposes.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where.

DETAILED DESCRIPTION

The disclosure extends to devices, methods and systems for obtaining an electrical conductance reading from a patient. Additionally, the disclosure relates to devices, systems, and methods for providing and using a probe having a tip or multiple tips that are used to facilitate in obtaining bioelectric readings from a patient for assessment, therapeutic and/or diagnostic purposes.

In the following description of the disclosure, reference is made to the accompanying drawings, which form a part hereof, and in which is shown by way of illustration specific implementations in which the disclosure is may be practiced. It is understood that other implementations may be utilized and structural changes may be made without departing from the scope of the disclosure.

Traditional medical science has long recognized certain electrical characteristics of humans and other living organisms. For example, the traditional medical community has recognized the electrical potentials generated by the human body in such forms as brain waves as detected by electroencephalographs (EEG), electrical impulses resulting from muscular heart activity as detected by electrocardiograms (EKG), and other electrical potentials measurable at other areas of the human body. While the relative levels of the electrical activity exhibit relatively small levels, such signals are nonetheless measurable and consistent.

In addition to measurable voltage levels, the human body and other mammalian organisms exhibit specific locations on the body wherein the conductance values are relatively predictable for healthy individuals. The locations of anatomical dermal conductance points exhibit a higher conductance value than normal surrounding tissue. Studies have indicated that many conductance points correspond to nerve innervations and trigger points. The conductance points are located under the skin (epidermis) and are accessed electrically through the skin either by the use of needles or by the using a probe tip pressed against the skin. As the outermost layer of epidermis (cornified layer) is less conducive, the probe tip may or may not need a fluid such as water or a type of electrode gel to enhance conductivity through the epidermis to the conductance point.

Interestingly, many of these conductance points match up with traditional acupuncture points. The representative conductance points and their relationship with organs and life systems of the human body have been characterized into more than 800 points that are organized into approximately 14 basic groups or meridians. The measurable state of these conductance points reflects the condition of the related meridians and therefore the health of organs and other functions of the human body. These conductance points are generally located at the extremity region of the hands and feet. The conductance value of normal healthy tissue at a conductance point for different individuals is generally in the same range. In at least some cases, when such tissue is inflamed or infected, the conductivity is higher than the normal range. Additionally, if the tissue is in a degenerative state, the conductivity may be lower.

Systems have been implemented to measure the conductance value at these conductance points and present conductance values to a clinician for use in diagnosing a condition. However, the traditional systems have proven difficult to use since the precise location of the points is difficult to locate and pinpoint. Furthermore, the differences in the characteristics of each patient and each point of a given patient can cause a practitioner to obtain inaccurate and/or unrepeatable readings. Moreover, current technologies have caused discomfort to a patient due to the number of times that a practitioner must take a conductance reading to isolate the correct location of the conductance point.

In some cases, even upon obtaining an accurate measurement at the right location, it can be difficult to correctly determine whether the measurement was accurate. In some systems, a first device is used to locate the points and a second device is brought in contact with the point to perform the conductance testing. While this technique is available, employing multiple devices introduces a potential for clinical error and is very time consuming. In addition, in every case the system used proves difficult to locate the points on the patient. The conductance testing may sometimes be compromised when the system does not accurately determine the points. Also, repeated testing of a certain point may cause the electrical potential of the point to be compromised.

Applicant recognized that challenges exist in the form of inaccurate readings, unrepeatable readings, pain, discomfort, examination time, and the like. Accordingly, it would be an improvement in the art to augment or even replace current devices and techniques.

Thus, in some aspects, the disclosure relates to obtaining bioelectric information. In particular, the disclosure relates to a device and methods for providing and using an enhanced probe device with a pressure regulated electrode tip and pressure sensor in obtaining a bioelectric conductance value from a patient for assessment, therapeutic and/or diagnostic purposes.

In some aspects, implementation of the disclosure takes place in association with a spring-loaded sensor head (tip) and actuator to regulate and control the force the tip applies to the skin. As the tip is pressed against the skin, the force of the tip pushing against the skin also creates a force pushing the tip against the probe device. To assist in governing the applied force, a spring is located between the tip and the probe device.

Another implementation is the utilization of a force sensor. To obtain an accurate reading, the technician must apply the correct amount of force. The force sensor confirms the correct amount of force. In addition, the force sensor allows for additional data to be collected from the patient. Due to the varying types of body type, the amount of force can significantly affect the reading. Having this additional data will improve the assessment of the patient.

These and other features and advantages of the disclosure will be set forth or will become more fully apparent in the description that follows and in the appended claims. Those skilled in the art will appreciate that the methods and processes can be used in association with a variety of different bioelectric sensing devices. Furthermore, the features and advantages of the disclosure may be learned by the practice of the disclosure or will be obvious from the description, as set forth hereinafter.

A detailed description of the devices, systems, and methods consistent with embodiments of the disclosure is provided below. While several embodiments are described, it should be understood that this disclosure is not limited to any one embodiment, but instead encompasses numerous alternatives, modifications, and equivalents. In addition, while numerous specific details are set forth in the following description in order to provide a thorough understanding of the embodiments disclosed herein, some embodiments may be practiced without some or all of these details. Moreover, for the purpose of clarity, certain technical material that is known in the related art has not been described in detail in order to avoid unnecessarily obscuring the disclosure.

In the flowing description of the disclosure, certain terminology is used for the purpose of reference only and is not intended to be limiting. Terms such as "upper," "lower," "above," and "below," refer to directions in the drawings to which reference is made. Terms such as "inward" and "outward" refer to directions towards and away from, respectively, the geometric center of the component described. Terms such as "side," "top," "bottom," "horizontal," "with in," "inside," and "vertical," describe the orientation of portions of the component within a consistent but arbitrary frame of reference which is made clear by reference to the text and the associated drawings describing the component under discussion. Such terminology includes words specifically mentioned above, derivatives thereof, and words of similar import.

Embodiments of the disclosure take place in association with a probe having a tip or multiple tips that are used to obtain a bioelectric value. In accordance with at least some embodiments of the disclosure, a patient may undergo bioelectric therapy corresponding to a condition diagnosed at an anatomical dermal conductance points which are known in the industry as meridian points. The various anatomical dermal conductance points are typically located throughout a patient's body. The dermal conductance points or meridian points aid the clinician in assessing and/or diagnosing a patient's condition and pinpointing a particular disorder.

Thus, while embodiments of the disclosure embrace a variety of different systems the current disclosure is a probe device having a tip or multiple tips. The tips, e.g., electrodes, are placed on an anatomical dermal conductance point. The conductance value is measured between the tip and a ground bar (hand mass) and is displayed on a conductance monitor or other output for evaluation by a clinician or practitioner. If the conductance value at a particular conductance point on the patient denotes an imbalance, the clinician may investigate the biological system meridian that corresponds to the conductance point presenting the imbalanced reading. Conversely, when a particular conductance point displays a balanced reading, the clinician thereafter measures the conductance at various other conductance points to properly assess and/or diagnose the condition of the patient.

Referring to FIG. 1 through FIG. 7 shows certain embodiments of the present device, where like reference numerals depict like components. A probe device 2 comprises a housing unit 12, a tip 4, a resilient member 30 and a force sensor 32. The housing unit 12 provides for a structure to attach the different components of the probe device 2 together. The housing unit 12 is made from any rigid material such as plastic. The shape of the housing unit 12 is such that it fits comfortably in a user's hand.

Figure 7:
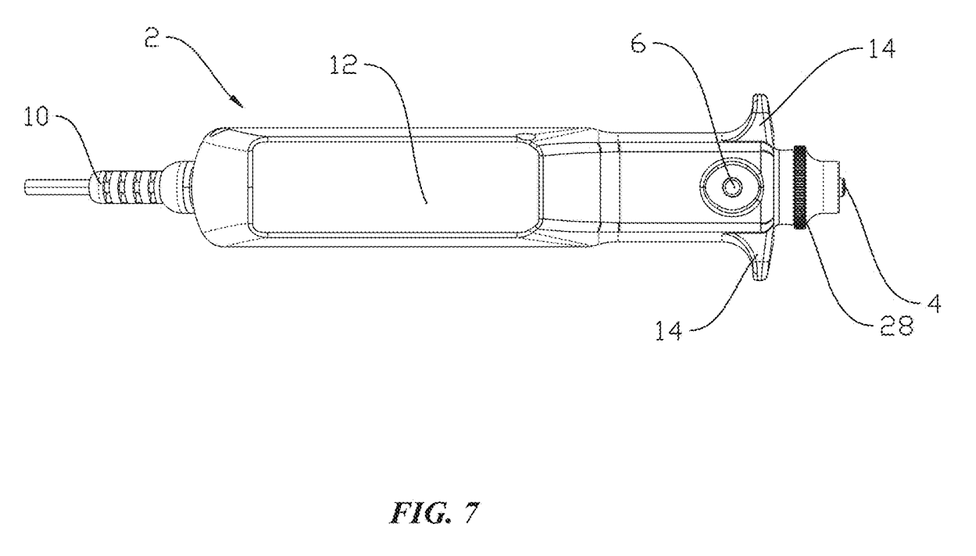
FIG. 7 illustrates a top view of the probe.
Figure 8:
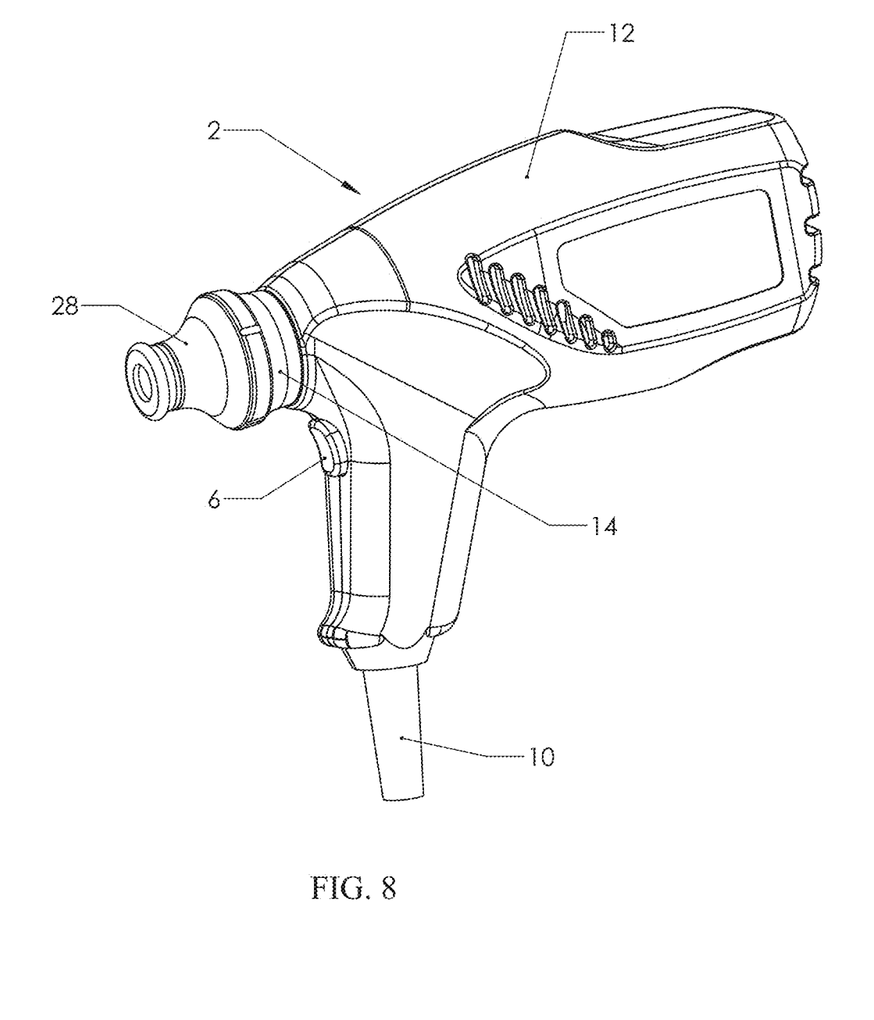
FIG. 8 is a probe with a trigger style switch in accordance with the teachings of the disclosure.

As perhaps best seen in FIG. 7, located near the front of the housing unit 12 are two finger levers 14. The finger levers 14 extend outwardly from the housing unit 12. In practice, the user will place the middle finger on one finger lever 14 and the index finger is free to activate the switch 6 and the thumb on the opposing finger lever 14. As the user pushes the probe device 2 against a patient's body, the finger levers 14 assist the user to easily apply the force necessary to operate the probe device 2. In another embodiment, as shown in FIG. 8, where the probe may have a trigger style switch, in practice, the user will place the index finger on one finger lever 14 and the middle finger pushes the switch 6 a thumb on the opposing finger lever 14. In an embodiment, the finger levers 14 can be incorporated into a hood 28, which is discussed further below.

Figure 3:
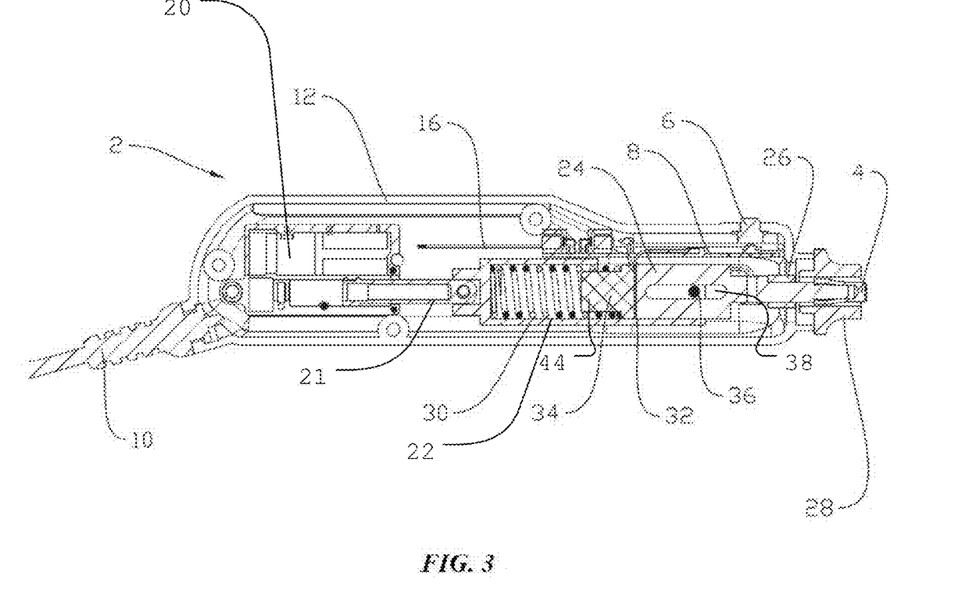
FIG. 3 illustrates a cross section of the probe in an activated mode; showing the linear actuator extended and applying a force to a spring backer which in turn applies force to the tip causing it to protrude through the hood, which illustrates a tip extended out of the probe.
Figure 4:
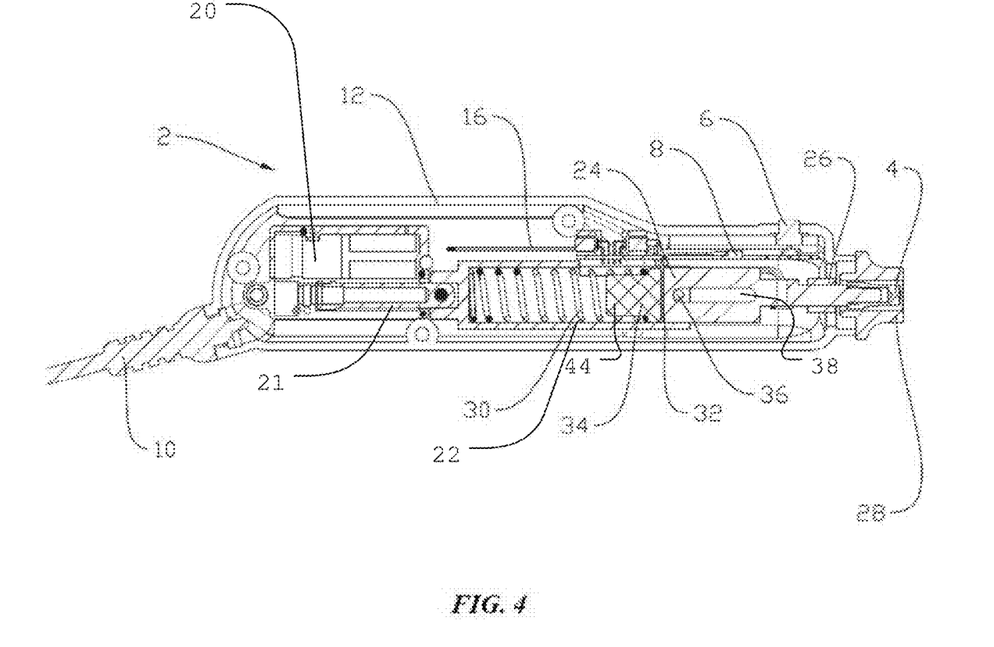
FIG. 4 illustrates a cross section of the probe in an inactive mode; showing a linear actuator retracted; in addition, the figure illustrates a tip withdrawn into the probe so that it is retracted into the hood.
Figure 5:
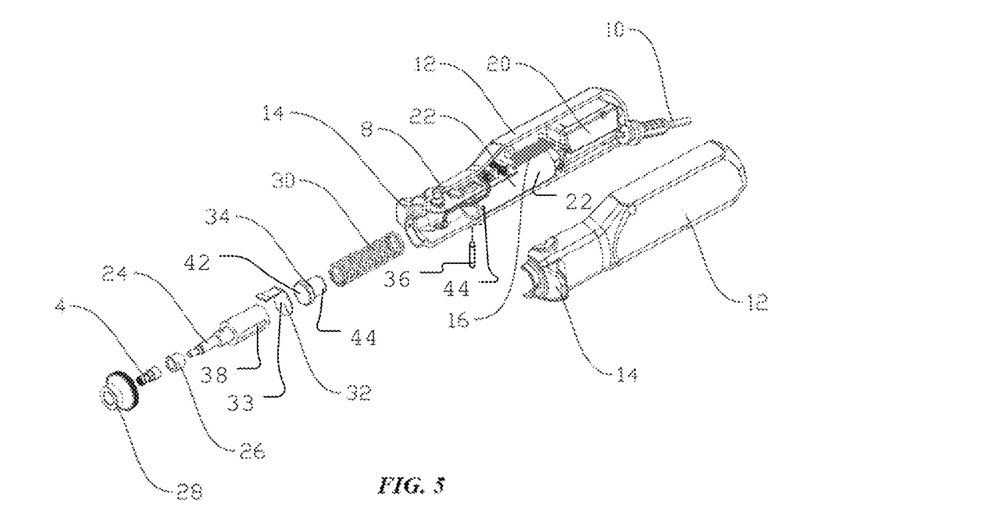
FIG. 5 illustrates an exploded prospective side elevation view of the probe showing the sequence of the components in the probe.
Figure 6:
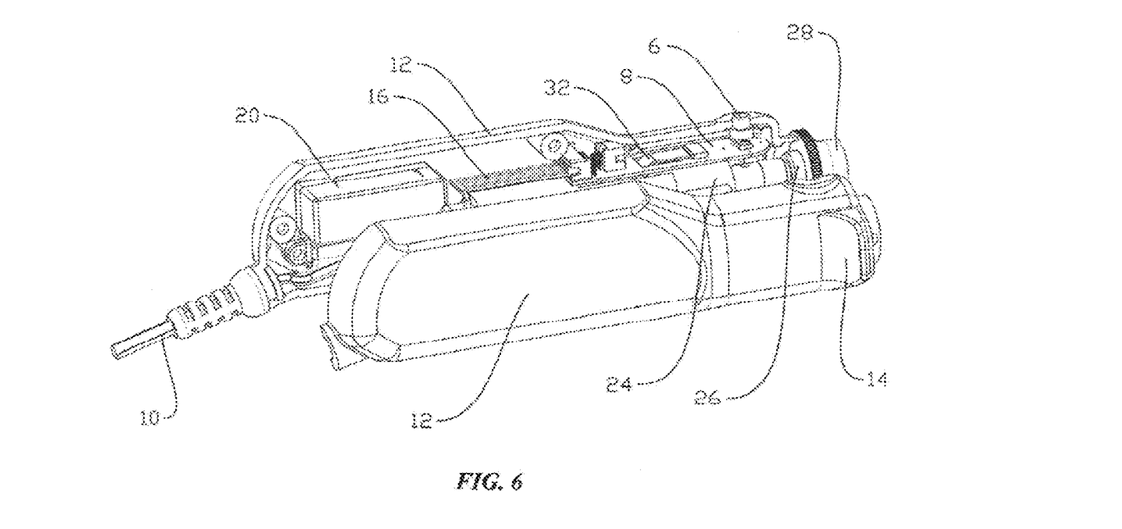
FIG. 6 illustrates a prospective side elevation view of the probe with one side of the housing unit partially removed.

As shown in FIGS. 3, 4, and 5 located at the front of the probe device 2 is the tip 4. The tip 4 may be an electrode tip, i.e., a conductor through which electricity (current) enters or leave an object, such as a patient. For example, the tip 4 is positioned at a meridian point and is pushed against a patient's dermal layer to obtain a bioelectrical conductance reading or measurement. The electrode tip 4 may be formed of brass, a brass alloy or brass plated metal. In practice, the tip 4 may be made of any material that will efficiently conduct an electrical signal.

Data regarding the electrical signal from the tip 4 is relayed to a computer processor (not shown) through a wire 16 and a cord 10. The computer processor evaluates the bioelectrical conductance data and records the data for future review and analysis. To protect and isolate the tip 4, the hood 28 is placed near or surrounds the location where the tip 4 extends from the probe device 2. Generally, the hood 28 can be easily removed from the probe device 2, to allow easy access to the tip 4.

As shown in FIGS. 3, 4, and 5, located near the back of the probe device 2 is the linear actuator 20. The linear actuator 20 creates motion in a straight line, which is generally the same as the longitudinal axis of the probe device 2. The linear actuator 20 comprises an output shaft 21. As illustrated in FIG. 3, when the probe device 2 is activated, the linear actuator 20 urges the tip 4 out of the probe device 2. As illustrated in FIG. 4, when the probe device 2 is not active, the linear actuator 20 pulls to the tip 4 into the probe device 2. While the linear actuator 20 shown is a simple one directional actuator, it is anticipated that several different types of actuators, rotational actuators or linear motors may be utilized.

As shown in FIGS. 3-5, interposed between the output shaft 21 of the linear actuator 20 and the tip 4 is a mechanical linkage. The mechanical linkage may comprise a spring backer 22, the resilient member 30, a force sensor backer 34, the force sensor 32 and a control shaft 24. When activated, the output shaft 21 of the linear actuator 20 applies a linear movement to the spring backer 22. The spring backer 22 moves along the same approximate longitudinal axis as the output shaft 21 of the linear actuator 20. The spring backer 22 transfers the force and movement of the linear actuator 20 to the resilient member 30.

Figure 1:
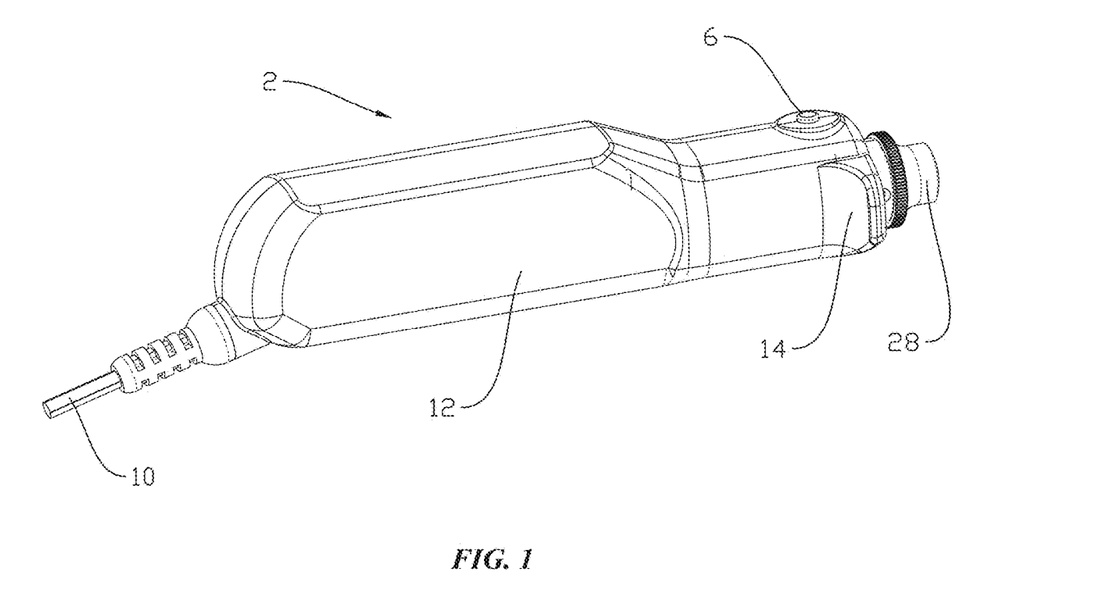
FIG. 1 is a prospective side elevation view of a probe.
Figure 2:
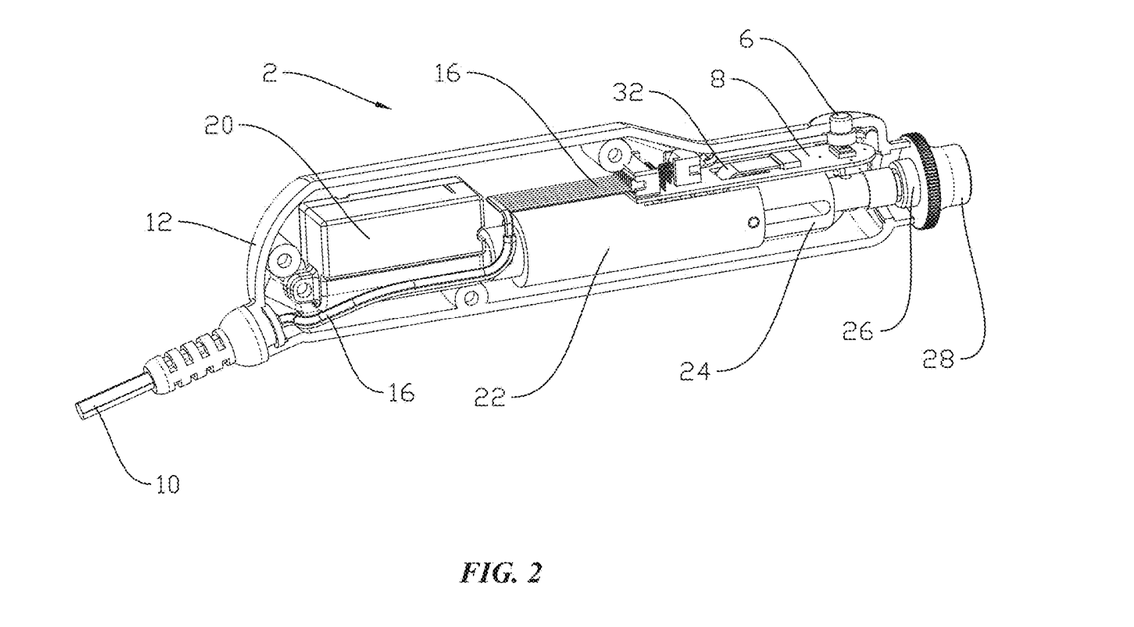
FIG. 2 illustrates a side view of the probe with a portion of a housing unit removed.

As best illustrated in FIGS. 2-4, the spring backer 22 is a simple elongated hollow and cylindrical tube with one closed end and one open end. The output shaft 21 of the linear actuator 20 is connected to the closed end of the spring backer 22 using a pin joint connection. The resilient member 30 is disposed within the interior of the spring backer 22 and abuts against the closed end. It will be appreciated that the spring backer 22 protects the resilient member 30 and prevents the resilient member 30 from kinking. The spring backer 22 is typically made of any ridged material, such as plastic or metal.

It will be appreciated that the resilient member 30 is used to regulate and maintain the pressure of the tip 4 against the dermal layer of the patient. That is, the resilient member 30 is biased against the tip 4 to maintain pressure on the dermal layer of the patient. While the resilient member 30 illustrated in the figures is a simple coiled spring, one skilled in the art will recognize that many varieties of devices and materials that may be supplemented for a coil compression spring including compressed air or gas. Other suitable devices may include a non-coil spring or a deformable material, such as rubber.

Referring to FIGS. 3-5, the linear actuator 20 applies a compression force and movement to the resilient member 30. As the resilient member 30 moves and is compressed, the resilient member 30 transfers the force and movement to the force sensor backer 34. As shown in FIG. 5, the force sensor backer 34 includes a front portion 40 having planar front surface 42 and a rearwardly extending plug 44. As seen in FIGS. 3 and 4, the plug 44 of the force sensor backer 34 is positioned within an interior passage of the resilient member 30.

Similar to the spring backer 22, the force sensor backer 34 ensures that the force of the resilient member 30 is distributed evenly. The resilient member 30 and the force sensor backer 34 are aligned along the same longitudinal axis. The front portion 40 of the force sensor backer 34 has a larger diameter than the resilient member 30, such that the resilient member 30 is supported and transfers the force to the force sensor backer 34. However, the diameter of the front portion 40 of the force sensor backer 34 is slightly smaller than the inner diameter of the interior passageway of the spring backer 22, such that the force sensor backer 34 can move smoothly and freely along the interior passage of the spring backer 22.

As shown in FIG. 5, inserted between the force sensor backer 34 and the control shaft 24 is a sensor pad 33 of the force sensor 32. It will be appreciated that the force sensor 32 measures the force between the force sensor backer 34 and the control shaft 24. Because of the mechanical linkage, this force is the same force the tip 4 applies to the skin or meridian point of a patient. Thus, the resilient member 30 is biased against the tip 4.

As will be explained in more detail hereinafter, the data from the force sensor 32 is relayed to a computer processor to help control the movement of the linear actuator 20 which regulates the compression of the resilient member 30 to govern the force that presses the tip 4 against the meridian point of the patient. The readings received from the tip 4 are processed for evaluation and the data is recorded. The force sensor 32 is a well know component to those skilled in the art and may take several different forms such as a force sensing resistor or a force sensing capacitor or a force sensitive load cell. That is, the pad 33 of the force sensor 32 may include a force sensitive resistor or a force sensitive capacitor or a force sensitive load cell.

As the force is transferred to the force sensor backer 34 from the resilient member 30 and linear actuator 20, the force and movement is transferred to the control shaft 24. The control shaft 24 transfers the force and movement of the linear actuator 20 to the tip 4. A linear guide bearing 26 assists the control shaft 24 to move smoothly along the same longitudinal axis as the probe device 2. The linear guide bearing 26 limits and controls the movement of the tip 4. In addition, the linear guide bearing 26 is mounted rigidly to the housing unit 12 which allow the control shaft 24 to move freely so that it is only controlled by the applied force of the resilient member 30.

Referring to FIGS. 3-5, located in the mid portion of the control shaft 24 is a rotation control groove 38. It will be appreciated that the rotation control groove 38 prevents the rotational movement of the control shaft 24. Generally, the tip 4 is attached to the control shaft 24 by screw thread. When a technician rotates the tip 4, the rotation control groove 38 prevents the rotation of the control shaft 24. The rotation control groove 38 receives a pin 36 that is installed into a bore 46 in the spring backer 22 (see FIG. 5). The pin 36 is simply long body that runs through the bore 46 from one side to the opposite side of the spring backer 22.

The width of the rotation control groove 38 is large enough for the pin 36 to move freely along the longitude axis of the probe device 2. The length of the rotation control groove 38 is such that when the linear actuator 20 is not active that the pin 36 contacts to the back of the rotation control groove 38 to withdraw the tip 4 into the probe device 2. When the linear actuator 20 is activated, the spring backer 22 pushes the pin 36 forward. However, the pin 36 does not necessarily contact the front of the rotation control groove 38.

Located at the front of the probe device 2 is the hood 28. The hood 28 is securely attached to the housing unit 12 and the linear bearing 26 so that it is isolated from all inputs and forces of all the internal components in the mechanical linkage, including the output shaft 21 of the linear actuator 20, spring backer 22, resilient member 30, force sensor backer 34, force sensor 32, control shaft 24, and tip 4.

When the probe device 2 is in use, the hood 28 is pressed against the patient's tissue so that it surrounds the meridian point being tested with greater force than is exerted to the tip 4 by the resilient member 30. By exerting a greater force than the resilient member 30, the hood 28 will remain in contact with the tissue surrounding the meridian point being tested. In the event that the exerted force is less than the applied force of the resilient member 30, the hood 28 will separate from the tissue and the test will no longer be controlled solely by the computerized device and test on that meridian will be invalid.

Located on the top of the probe device 2 is a switch 6. As shown in FIG. 4, the switch 6 activates a variety of functions. There are several different varying types of switches 6 that may be utilized. In addition, the location of the switch 6 on the probe device 2 may vary.

As shown in FIG. 2, to provide electrical power and to relay bio-conductance and force data to a computing device, the probe device 2 is connected to the cord 10. The cord 10 is a typical electrical cord with metal wires that easily conducts an electrical signal and electricity. The metal wires are coated in a material that insulates and protects the metal wires. One skilled in the art will recognize that the electrical power to the probe device 2 could be supplied by a battery. The conductivity data obtained from the tip 4 as well as the force data obtained by the force sensor 32 can be transmitted over a wire or wirelessly to a computer processor as will be explained in more detail hereinafter.

The probe device 2 may further comprise a circuit board 8 having a processor (not shown) mounted thereon. The processor may run firmware associated with the operation of the probe device 2 as described herein. The actuator 20, the force sensor 32, switch 6, and the tip 4 may be connected to, and communicate with, the processor. The processor, in turn, may be connected to an external computing device. The processor may control the actuator 20 responsive to control signals received from a computing device. The processor may receive force data from the force sensor 32 and transmit the force data to the computing device. The processor may power the probe device 2 in response to user activation of the switch. The processor may receive bio-conductance data from the tip 4 and transmit the bio-conductance data to the computing device. It will be appreciated that the bio-conductance data may be a current or voltage measurement taken at the tip 4.

Figure 9:
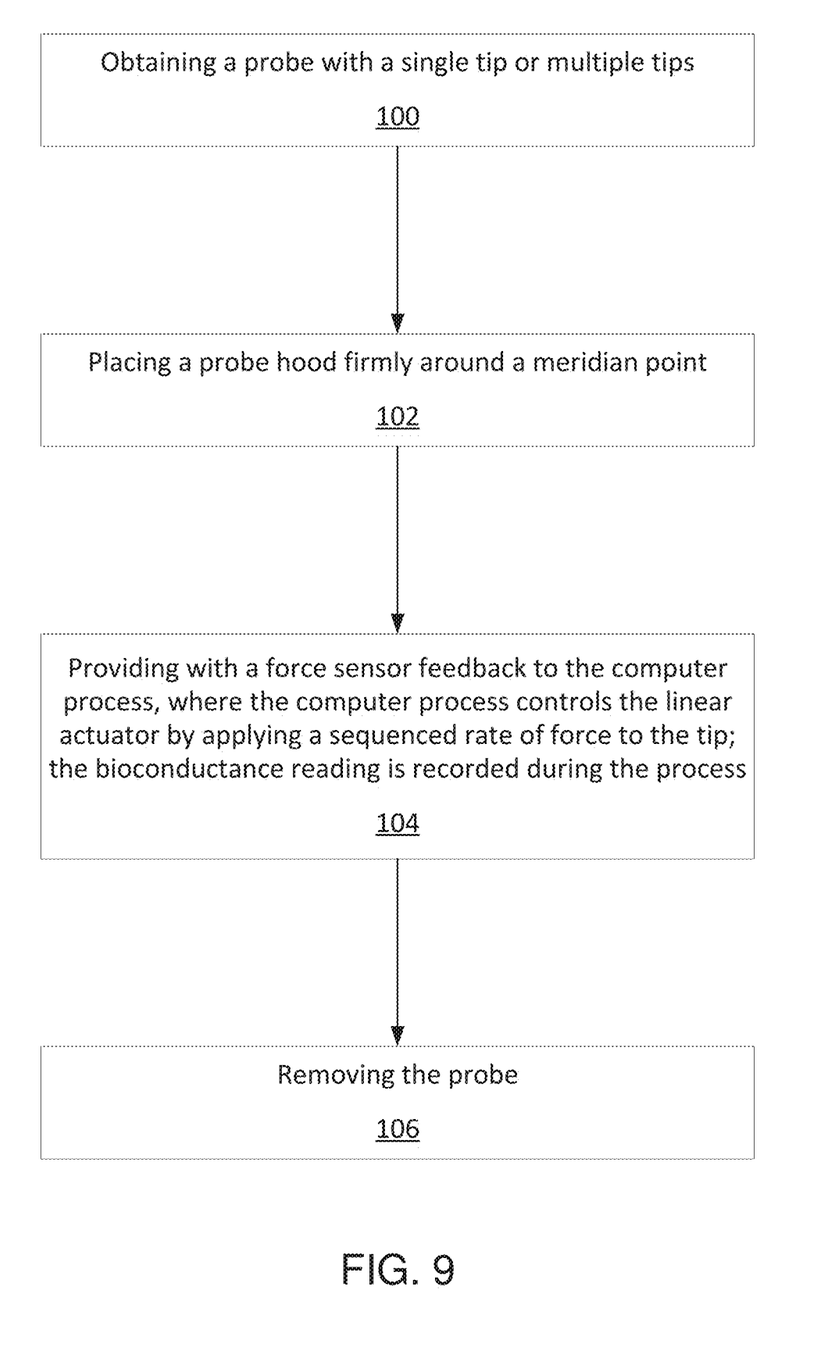
FIG. 9 is a flow diagram illustrating the steps of utilizing the probe and force sensing resistor in accordance with the teachings of the disclosure.

In operation, a user will provide a computer device connected to a probe device 2 (step 100). The user places the probe device 2 on a meridian or acupressure point located on a patient such that hood 28 surrounds the meridian point (step 102). To insure the probe device 2 is placed firmly against the patient's skin, the user will utilize the finger levers 14 to press with a level of force greater than what the compressed resilient member 30 will apply through the test cycle.

The linear actuator 20 applies a controlled force and movement such that the tip 4 extends out of the probe device 2 (step 104). As the tip 4 presses against the patient's skin, the force sensor 32 measures the force of the tip 4 and aids the computer device in controlling the force applied to tip 4 through the test cycle. The tip 4 reads or measures the bioelectric conductance values through the test cycle (step 106). The conductance data is then transferred to a computer process for analysis and recording. The probe device 2 is removed from the patient (step 108) and the linear actuator 20 resets so that the probe device 2 is ready for the next test cycle.

Figure 11:
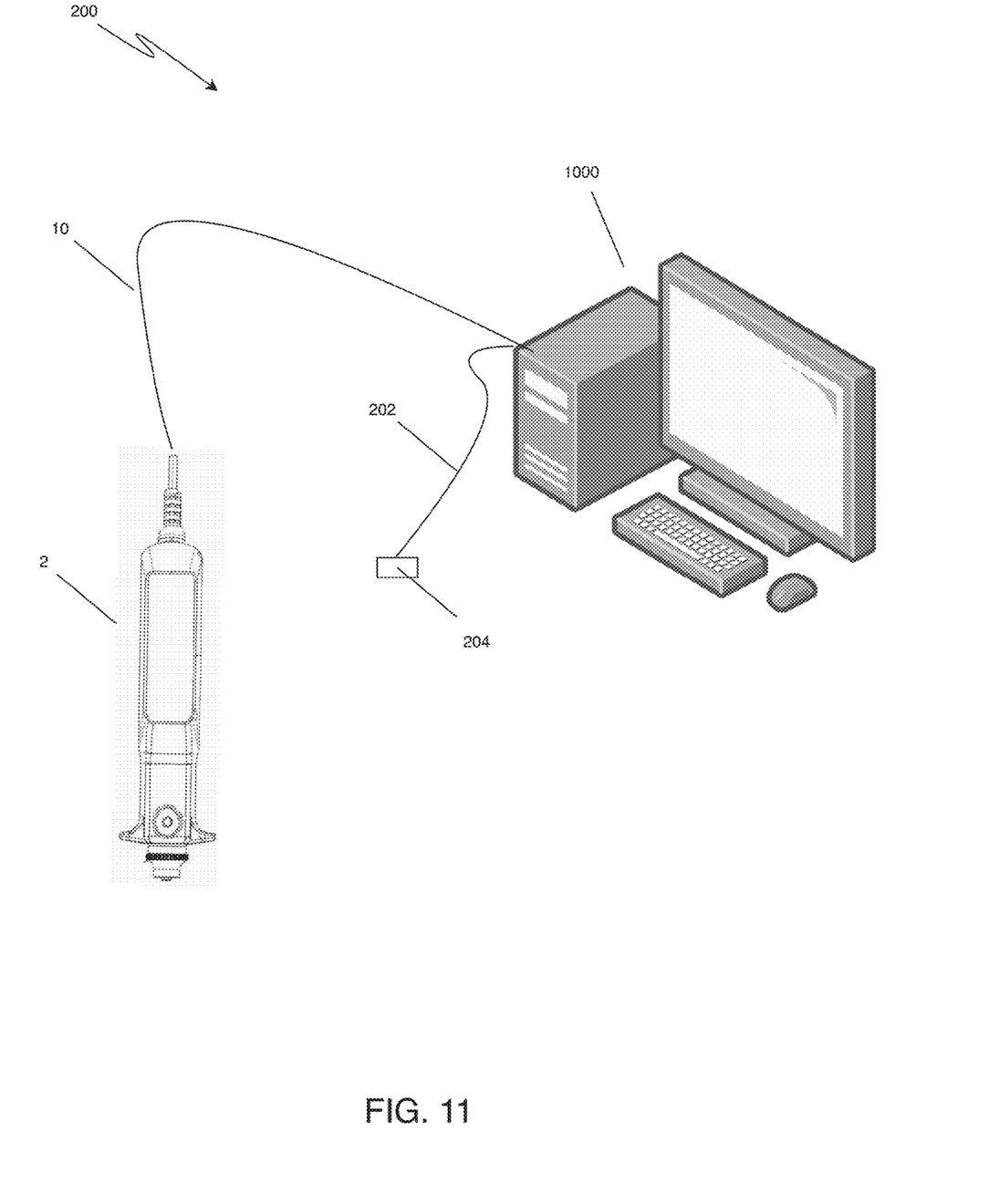
FIG. 11 is a diagram of an exemplary system for measuring the bio-conductance of a patient.

Referring now to FIG. 11, there is depicted a system 200 for obtaining bio-conductance readings from a patient. The system 200 includes a probe device 2 connected to a computing device 1000. The computing device 1000 may include a display, input devices such as a keyboard and mouse, and a housing having a processor and memory contained therein. The probe device 2 and the computing device 1000 are connected by a cord 10. Alternatively, the probe device 2 and the computing device 1000 are connected by a wireless connection, such as Bluetooth or Wi-Fi. The probe device 2 and the computing device 1000 may communicate over the connection. For example, the computing device 1000 may send and receive data to and from the probe device 2. The system 200 may further comprise a reference electrode 204 connected to the computing device 1000 by a cord 202. It will be appreciated that the reference electrode 204 is placed against the patient's skin such that a current may pass between the electrode tip 4 of the probe device 2 and the reference electrode 204 (through the patient).

Figure 10:
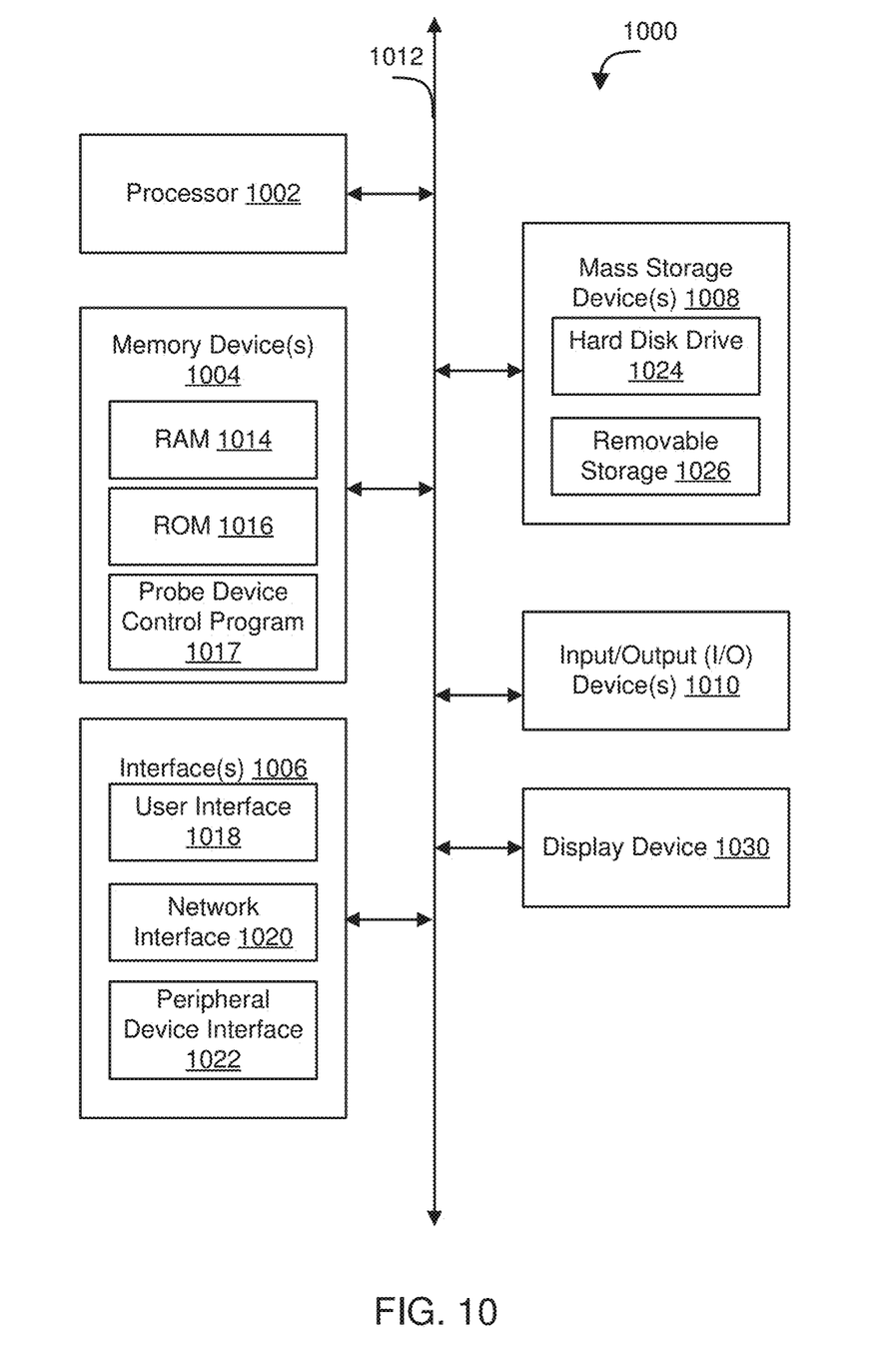
FIG. 10 is a block diagram of an example computing device in accordance with the teachings of the disclosure.

Referring now to FIG. 10, there is depicted a block diagram of an exemplary configuration of the computing device 1000. Computing device 1000 may be used to perform various procedures, such as receiving data from the probe device 2 and controlling the probe device 2. In one embodiment, the computing device 1000 can function as a computing system, control unit, or the like. Computing device 1000 can perform various monitoring functions as discussed herein, and can execute one or more application programs, such as application programs to receive data from the probe device 2 and to control the features of the probe device 2. The computing device 1000 can be any of a wide variety of computing devices, such as a microprocessor, laptop computer, desktop computer, in-dash computer, vehicle control system, a notebook computer, a server computer, a handheld computer, tablet computer and the like.

Computing device 1000 includes one or more processor(s) 1002, one or more memory device(s) 1004, one or more interface(s) 1006, one or more mass storage device(s) 1008, one or more Input/Output (I/O) device(s) 1010, and a display device 1030 all of which are coupled to a bus 1012. Processor(s) 1002 include one or more processors or controllers that execute instructions stored in memory device(s) 1004 and/or mass storage device(s) 1008. Processor(s) 1002 may also include various types of computer-readable media, such as cache memory.

Memory device(s) 1004 include various computer-readable media, such as volatile memory (e.g., random access memory (RAM) 1014) and/or nonvolatile memory (e.g., read-only memory (ROM) 1016). Memory device(s) 1004 may also include rewritable ROM, such as Flash memory.

Mass storage device(s) 1008 include various computer readable media, such as magnetic tapes, magnetic disks, optical disks, solid-state memory (e.g., Flash memory), and so forth. As shown in FIG. 10, a particular mass storage device is a hard disk drive 1024. Various drives may also be included in mass storage device(s) 1008 to enable reading from and/or writing to the various computer readable media. Mass storage device(s) 1008 include removable media 1026 and/or non-removable media.

I/O device(s) 1010 include various devices that allow data and/or other information to be input to or retrieved from computing device 1000. Example I/O device(s) 1010 include cursor control devices, keyboards, keypads, microphones, monitors or other display devices, speakers, printers, network interface cards, modems, and the like.

Display device 1030 includes any type of device capable of displaying information to one or more users of computing device 1000. Examples of display device 1030 include a monitor, display terminal, video projection device, and the like.

Interface(s) 1006 include various interfaces that allow computing device 1000 to interact with other systems, devices, or computing environments. Example interface(s) 1006 may include any number of different network interfaces 1020, such as interfaces to local area networks (LANs), wide area networks (WANs), wireless networks, and the Internet. Other interface(s) include user interface 1018 and peripheral device interface 1022. The interface(s) 1006 may also include one or more user interface elements 1018. The interface(s) 1006 may also include one or more peripheral interfaces such as interfaces for printers, pointing devices (mice, track pad, or any suitable user interface now known to those of ordinary skill in the field, or later discovered), keyboards, and the like.

Bus 1012 allows processor(s) 1002, memory device(s) 1004, interface(s) 1006, mass storage device(s) 1008, and I/O device(s) 1010 to communicate with one another, as well as other devices or components coupled to bus 1012. Bus 1012 represents one or more of several types of bus structures, such as a system bus, PCI bus, IEEE bus, USB bus, and so forth.

For purposes of illustration, programs and other executable program components are shown herein as discrete blocks, although it is understood that such programs and components may reside at various times in different storage components of computing device 1000, and are executed by processor(s) 1002. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Loaded into the memory device 1004 is a probe device control ("PDC") program 1017. The PDC program 1017 contains computer-readable instructions that are executable by the processor 1002. The PDC program 1017 allows the processor 1002 of the computing device 1000 to interface with the probe device 2. The PDC program 1017 may allow the processor 1002 of the computing device 1000 to receive conductance data obtained by the tip 4 of the probe device 2. In addition, the PDC program 1017 allows the processor 1002 to control the operation of the linear actuator 20. That is, the PDC program 1017 allows the processor 1002 to send control signals to cause the tip 4 to be extended or retracted from the probe device 2.

The PDC program 1017 may include an initial test sequence routine. In the initial test sequence routine, the processor 1002, executing the computer-readable instructions of the PDC program 1017, causes the tip 4 to be fully extended so that it is extended out of the hood 28 and so that it can make contact with a meridian on the test subject and complete the test circuit to take a conductance reading. When the system 200 establishes a complete circuit, the processor 1002 immediately retracts the tip 4 fully into the hood 28 so that it no longer contacts the meridian point and breaks the test circuit. The processor 1002 then extends the tip 4 so that it again protrudes out of the hood 28 and contacts the meridian point.

This time the force that the tip 4 exerts against the meridian point is controlled with feedback from conductance data being received by the processor 1002. That is, the probe device 2 sends conductance data from the tip 4 to the processor 1002. The processor 1002 analyses the conductance data and then sends control signals to control the force and rate of force at the tip 4 so that the test results are optimized. That is, the force exerted by the resilient member 30 is precisely manipulated by the processor 1002 to control the compression of the resilient member 30 with the linear actuator 20. The more the resilient member 30 is compressed by the linear actuator 20, the more force is exerted by the tip 4 on the patient.

The force sensor 32 verifies and helps control the compression of the resilient member 30—which aids in the accuracy and repeatability of the bio-conductance measurements. That is, the force data gathered by the force sensor 32 is provided to the processor 1002. The processor 1002 then uses the force data and the bio-conductance data to control the actuator 20 of the probe device 2 to vary the force of the tip 4. Using the above procedure, the processor 1002 ensures data consistency in a patient's bio-conductance readings.

Examples

The following examples pertain to further embodiments.

Example 1 is a device for measuring bio-conductance. The device comprises an actuator having an output shaft. The device further comprises an electrode tip. The device further comprises a mechanical linkage interconnecting the output shaft and the electrode tip. The mechanical linkage comprises a resilient member biased against the electrode tip. The resilient member exerts a variable force on the electrode tip responsive to a position of the output shaft of the actuator.

In Example 2, the device of Example 1 further comprises a force sensor in communication with the electrode tip. As used herein, the term "in communication with" means that the force sensor is able to measure a force at, or applied to, the electrode tip.

In Example 3, the device of any of Examples 1 or 2, where the force sensor comprises a sensor pad interposed in the mechanical linkage between the electrode tip and the output shaft.

In Example 4, the device of any of Examples 1-3, where the force sensor comprises one of a force sensitive resistor or a force sensitive capacitor or a force sensitive load cell.

In Example 5, the device of any of Examples 1-4, where the resilient member is one of a spring, a coil spring, and a deformable material.

In Example 6, the device of any of Examples 1-5, wherein the actuator is a linear actuator.

In Example 7, the device of any of Examples 1-6, further comprising a hood, wherein the electrode tip is operable between a retracted position and an extended position with respect to the hood and in response to movement of the output shaft of the actuator.

In Example 8, the device of any of Examples 1-7, where the mechanical linkage is responsive to movement of the output shaft of the actuator to control a force applied at the electrode tip.

In Example 9, the device of any of Examples 1-8, where the mechanical linkage further comprises a hollow cylindrical tube extending between a closed end and an open end; where the resilient member is disposed within the hollow cylindrical tube; and where the output shaft of the actuator is connected to the closed end of the hollow cylindrical tube.

In Example 10, the device of any of Examples 1-9, where the mechanical linkage further comprises a control shaft and a pin; where the control shaft is interposed between the electrode tip and the resilient member; where the control shaft comprises a rotation control groove; where the pin connects the control shaft and the hollow cylindrical tube; where the pin extends through a bore in a sidewall of the hollow cylindrical tube and the rotation control groove of the control shaft.

In Example 11, the device of any of Examples 1-10, further comprising a force sensor having a sensing pad; where the sensing pad of the force sensor is interposed between the control shaft and the resilient member.

In Example 12, the device of any of Examples 1-11, where the mechanical linkage further comprises a force sensor backer; the force sensor backer having a top surface and a plug extending rearwardly from the top surface; where the force sensor backer is disposed within the hollow cylindrical tube; where the resilient member comprises an inner passage; where the plug of the force sensor backer extends into the inner passage of the resilient member; where the sensing pad of the force sensor is disposed between the control shaft and the top surface of the force sensor backer.

Example 13 is a system for measuring bio-conductance that comprises an actuator having an output shaft; an electrode tip; a mechanical linkage interconnecting the output shaft and the electrode tip, the mechanical linkage comprising a resilient member biased against the electrode tip; and a processor and a memory, the memory having computer-executable instructions stored therein that, when executed, cause the processor to vary a position of the output shaft of the actuator responsive to conductance data obtained from the electrode tip to thereby vary a compression of the resilient member and the force applied by the resilient member to the electrode tip.

In Example 14, the system of Example 13, further comprising a force sensor in communication with the electrode tip and the processor, wherein the force sensor provides force data to the processor regarding the force applied at the electrode tip.

In Example 15, the system of any one of Examples 13 and 14, wherein the force sensor comprises a pad interposed between the electrode tip and the output shaft.

In Example 16, the system of any one of Examples 13-15, where the force sensor comprises a force sensitive resistor or a force sensitive capacitor or a force sensitive load cell.

In Example 17, the system of any one of Examples 13-16, where the actuator is a linear actuator.

In Example 18, the system of any one of Examples 13-17, where the mechanical linkage further comprises a hollow cylindrical tube extending between a closed end and an open end; where the resilient member is disposed within the hollow cylindrical tube; where the output shaft of the actuator is connected to the closed end of the hollow cylindrical tube.

In Example 19, the system of any one of Examples 13-18, further comprising a force sensor having a sensing pad; where the mechanical linkage further comprises a control shaft and a pin; where the control shaft is interposed between the electrode tip and the resilient member; where the control shaft comprises a rotation control groove; where the pin connects the control shaft and hollow cylindrical tube; where the pin extends through a bore in a sidewall of the hollow cylindrical tube and the rotation control groove of the control shaft.

Example 20 is a method of measuring conductance of an object comprising: (A) providing a probe device having (i) an actuator having an output shaft, (ii) an electrode tip, and (iii) a mechanical linkage interconnecting the output shaft and the electrode tip, the mechanical linkage comprising a resilient member that exerts a force at the electrode tip responsive to a position of the output shaft; (B) placing the electrode tip of the probe device against the object; and (C) controlling the force the resilient member exerts at the electrode tip by signaling the actuator to vary a position of the output shaft.

Various techniques, or certain aspects or portions thereof, may take the form of program code (i.e., instructions) embodied in tangible media, such as floppy diskettes, CD-ROMs, hard drives, a non-transitory computer readable storage medium, or any other machine readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network. The components may be passive or active, including agents operable to perform desired functions.

Reference throughout this specification to "an example" means that a particular feature, structure, or characteristic described in connection with the example is included in at least one embodiment of the present disclosure. Thus, appearances of the phrase "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present disclosure may be referred to herein along with alternatives for the various components thereof. It is understood that such embodiments, examples, and alternatives are not to be construed as de facto equivalents of one another, but are to be considered as separate and autonomous representations of the present disclosure.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered illustrative and not restrictive.

Those having skill in the art will appreciate that many changes may be made to the details of the above-described embodiments without departing from the underlying principles of the disclosure. The scope of the present disclosure should, therefore, be determined only by the following claims. The disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

What is claimed:

1. A device for measuring bio-conductance comprising:
   an actuator comprising an output shaft, wherein, when activated, the actuator drives the output shaft in a linear direction;
   an electrode tip; and
   a mechanical linkage comprising a resilient member that biases the electrode tip, wherein the resilient member is disposed between the output shaft of the actuator and the electrode tip;
   wherein the resilient member exerts a variable force on the electrode tip responsive to a position of the output shaft; and
   wherein the actuator regulates compression of the resilient member by movement of the output shaft to adjust the variable force the resilient member exerts on the electrode tip.

2. The device of claim 1, further comprising a force sensor in communication with the electrode tip.

3. The device of claim 2, wherein the force sensor comprises a sensor pad interposed in the mechanical linkage between the electrode tip and the output shaft.

4. The device of claim 2, wherein the force sensor comprises one of a pressure sensitive resistor and a pressure sensitive capacitor.

5. The device of claim 1, wherein the resilient member is one of a spring, a coil spring, and a deformable material.

6. The device of claim 1, wherein the actuator is a linear actuator.

7. The device of claim 1, further comprising a hood, wherein the electrode tip is operable between a retracted position and an extended position with respect to the hood.

8. The device of claim 1, wherein the mechanical linkage is responsive to movement of the output shaft of the actuator to control a force applied at the electrode tip.

9. The device of claim 1,
   wherein the mechanical linkage further comprises a hollow cylindrical tube extending between a closed end and an open end;
   wherein the resilient member is disposed within the hollow cylindrical tube;
   wherein the output shaft of the actuator is connected to the closed end of the hollow cylindrical tube.

10. The device of claim 9,
    wherein the mechanical linkage further comprises a control shaft and a pin;
    wherein the control shaft is interposed between the electrode tip and the resilient member;
    wherein the control shaft comprises a rotation control groove;
    wherein the pin connects the control shaft and the hollow cylindrical tube;
    wherein the pin extends through a bore in a sidewall of the hollow cylindrical tube and the rotation control groove of the control shaft.

11. The device of claim 10, further comprising a force sensor having a sensing pad;
    wherein the sensing pad of the force sensor is interposed between the control shaft and the resilient member.

12. The device of claim 11,
    wherein the mechanical linkage further comprises a force sensor backer;
    the force sensor backer having a top surface and a plug extending rearwardly from the top surface;
    wherein the force sensor backer is disposed within the hollow cylindrical tube;
    wherein the resilient member comprises an inner passage;
    wherein the plug of the force sensor backer extends into the inner passage of the resilient member;
    wherein the sensing pad of the force sensor is disposed between the control shaft and the top surface of the force sensor backer.

13. A system for measuring bio-conductance comprising:
    an actuator comprising an output shaft, wherein, when activated, the actuator drives the output shaft in a linear direction;
    an electrode tip;
    a mechanical linkage-comprising a resilient member that biases the electrode tip, wherein the resilient member is disposed between the output shaft of the actuator and the electrode tip; and
    a processor and a memory, the memory having computer-executable instructions stored therein that, when executed, cause the processor to vary a position of the output shaft of the actuator responsive to conductance data obtained from the electrode tip; and wherein the actuator regulates compression of the resilient member by movement of the output shaft to adjust the variable force the resilient member exerts on the electrode tip.

14. The system of claim 13, further comprising a force sensor in communication with the electrode tip and the processor, wherein the force sensor provides force data to the processor regarding the force applied to the electrode tip.

15. The system of claim 14, wherein the force sensor comprises a pad interposed between the electrode tip and the output shaft.

16. The system of claim 14, wherein the force sensor comprises a pressure sensitive resistor or a pressure sensitive capacitor.

17. The system of claim 13, wherein the actuator is a linear actuator.

18. The system of claim 13,
wherein the mechanical linkage further comprises a hollow cylindrical tube extending between a closed end and an open end;
wherein the resilient member is disposed within the hollow cylindrical tube;
wherein the output shaft of the actuator is connected to the closed end of the hollow cylindrical tube.

19. The system of claim 18,
wherein the mechanical linkage further comprises a control shaft and a pin;
wherein the control shaft is interposed between the electrode tip and the resilient member;
wherein the control shaft comprises a rotation control groove;
wherein the pin connects the control shaft and hollow cylindrical tube;
wherein the pin extends through a bore in a sidewall of the hollow cylindrical tube and the rotation control groove of the control shaft.

20. A method of measuring conductance of an object comprising:
providing a probe device having (i) an actuator comprising an output shaft, wherein, when activated, the actuator drives the output shaft in a linear direction, (ii) an electrode tip, and (iii) a mechanical linkage comprising a resilient member that biases the electrode tip, wherein the resilient member is disposed between the output shaft of the actuator and the electrode tip, and wherein the resilient member exerts a force at the electrode tip responsive to a position of the output shaft;
placing the electrode tip of the probe device against the object; and
controlling the force the resilient member exerts against the electrode tip by signaling the actuator to vary a position of the output shaft;
wherein the actuator regulates compression of the resilient member by movement of the output shaft to adjust the variable force the resilient member exerts on the electrode tip.

* * * * *